United States Patent
Arsenin et al.

(10) Patent No.: US 10,962,536 B2
(45) Date of Patent: Mar. 30, 2021

(54) BIOLOGICAL SENSOR AND A METHOD OF THE PRODUCTION OF BIOLOGICAL SENSOR

(71) Applicant: MOSCOW INSTITUTE OF PHYSICS AND TECHNOLOGY (STATE UNIVERSITY), Dolgoprudny (RU)

(72) Inventors: Alexey Vladimirovich Arsenin, Moscow (RU); Yury Viktorovich Stebunov, Ivanteevka (RU)

(73) Assignee: MOSCOW INSTITUTE OF PHYSICS AND TECHNOLOGY (STATE UNIVERSITY), Dolgoprudny (RU)

( * ) Notice: Subject to any disclaimer, the term of this patent is extended or adjusted under 35 U.S.C. 154(b) by 277 days.

(21) Appl. No.: 15/671,187

(22) Filed: Aug. 8, 2017

(65) Prior Publication Data
US 2017/0336401 A1     Nov. 23, 2017

Related U.S. Application Data

(62) Division of application No. 14/647,397, filed as application No. PCT/RU2013/001100 on Dec. 9, 2013, now abandoned.

(30) Foreign Application Priority Data

Feb. 20, 2013    (RU) ................................ 2013107267

(51) Int. Cl.
    *G01N 33/553*     (2006.01)
    *B82Y 40/00*     (2011.01)
    (Continued)

(52) U.S. Cl.
    CPC ............ *G01N 33/553* (2013.01); *B82Y 15/00* (2013.01); *C23C 14/30* (2013.01);
    (Continued)

(58) Field of Classification Search
None
See application file for complete search history.

(56) References Cited

U.S. PATENT DOCUMENTS

| | | |
|---|---|---|
| 5,242,828 A | 9/1993 | Bergstrom et al. |
| 5,763,191 A | 6/1998 | Knoll et al. |
| (Continued) | | |

FOREIGN PATENT DOCUMENTS

| | | |
|---|---|---|
| EP | 2 216 642 A1 | 8/2010 |
| GB | 2459604 B | 7/2011 |
| (Continued) | | |

OTHER PUBLICATIONS

Stebunov et al. ("Superior Sensitivity of Copper-based plasnnonic biosensors", Langmuir, 2018, 34, 4681-4687 (Year: 2018).*
(Continued)

*Primary Examiner* — Tracy Vivlemore
*Assistant Examiner* — Nam P Nguyen
(74) *Attorney, Agent, or Firm* — Seckel IP, PLLC

(57) ABSTRACT

The invention is related to the field of biotechnology, specifically to the investigation of biomolecular interactions and sensing of biomolecules using a surface plasmon resonance. The biological sensor and a method of its production based on the thin films of graphene, graphene oxide, or single-walled or multi-walled carbon nanotubes are described.

Figure 1:
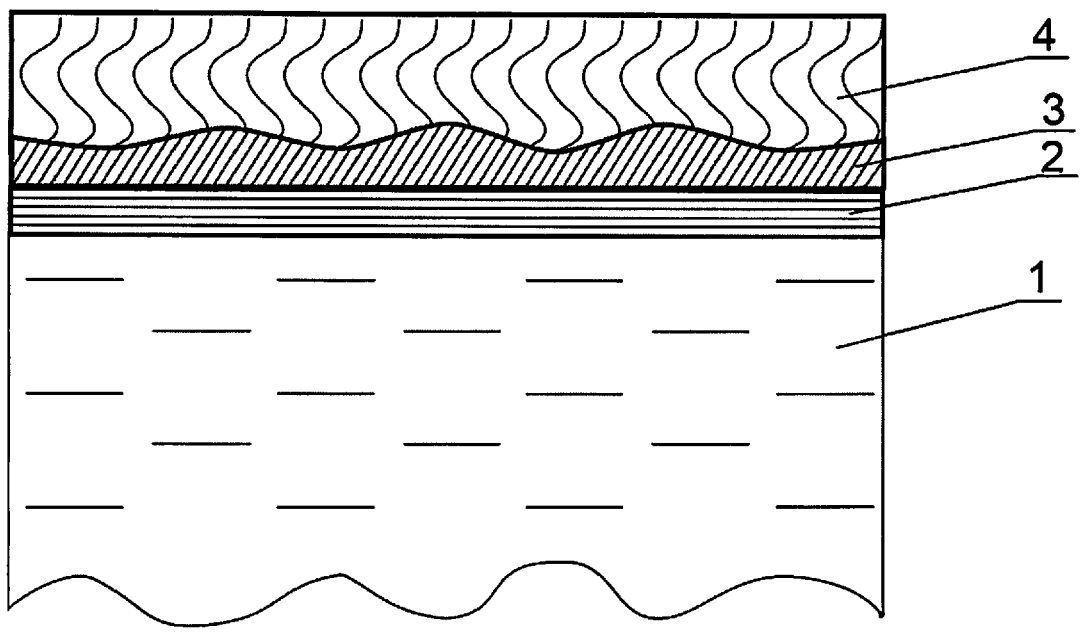

The technical results of the invention are a high sensitivity of the biosensor in combination with a high biospecificity; an expansion of the range of device applications; the protection of the metal film from an environmental exposure; the possibility to detect large biological objects.

(Continued)

The proposed device and method of its production can be used for monitoring and recording of the concentration of chemical and biochemical substances and for the definition of parameters of biomolecular reactions in different industrial processes using biological materials, the invention can be also used in the pharmaceutical industry for the investigation of pharmacological properties and for the determination of a chemical composition of developing drugs, and also it can be used in processes of quality control of food products.

15 Claims, 6 Drawing Sheets

(51) Int. Cl.
    *G01N 33/551*      (2006.01)
    *B82Y 15/00*      (2011.01)
    *C23C 14/30*      (2006.01)
    *G01N 33/543*      (2006.01)

(52) U.S. Cl.
    CPC ..... *G01N 33/54373* (2013.01); *G01N 33/551* (2013.01); *B82Y 40/00* (2013.01)

(56) References Cited

U.S. PATENT DOCUMENTS

| | | | |
|---|---|---|---|
| 2007/0065954 A1* | 3/2007 | Taya | B82Y 15/00 436/524 |
| 2009/0116020 A1 | 5/2009 | Wu et al. | |
| 2011/0037033 A1* | 2/2011 | Green | B03D 3/00 252/510 |
| 2012/0114558 A1 | 5/2012 | Stojanovic | |
| 2013/0011914 A1 | 1/2013 | Kim | |

FOREIGN PATENT DOCUMENTS

| | | |
|---|---|---|
| RU | 2379671 C1 | 1/2010 |
| WO | 2011/004136 A1 | 1/2011 |

OTHER PUBLICATIONS

Wu et al. (Optics Express, vol. 18, No. 14, pp. 14395-14400, published Jun. 21, 2010) (Year: 2010).*
Canadian Office Action dated Jun. 5, 2017 in corresponding Canadian application No. 2,935,101 (in English, 3 pages).
Blake et al., "Making Graphene Visible", Appl. Phys. Letters, vol. 91, pp. 063124-1 to 063124-3, 2007 (in English; cited in parent U.S. Appl. No. 14/647,397).
Guan et al., "Smallest carbon nanotube assigned with atomic resolution accuracy", Nano Letters, vol. 8(2), pp. 459-462, 2008 (in English; cited in parent U.S. Appl. No. 14/647,397).
Pandey et al., "Scanning probe microscopy study of exfoliated oxidized graphene sheets", Surface Science, vol. 602(9), pp. 1607-1613, 2008 (in English; cited in parent U.S. Appl. No. 14/647,397).
Schasfoort et al., "SPR Instrumentation", Chapter 3 in "Handbook of surface plasmon resonance", Royal Society of Chemistry, pp. 35-80, 2008 (in English; cited in parent U.S. Appl. No. 14/647,397).
Wijaya et al., "Graphene-based high-performance surface plasmon resonance biosensors", Proc. SPIE 8424, Nanophotonics IV, pp. 84240R1-84240R7, 2012 (in English; cited in parent U.S. Appl. No. 14/647,397).
Geim et al., "The rise of graphene", Nature Materials, vol. 6, pp. 183-191, Mar. 2007 (in English; cited in parent U.S. Appl. No. 14/647,597).
Mateescu et al., "Thin Hydrogel Films for Optical Biosensor Application", Membranes, vol. 2, pp. 40-69, published Feb. 8, 2012 (in English; cited in parent U.S. Appl. No. 14/647,397).
Caldwell et al., "Technique for the Dry Transfer of Epitaxial Graphene onto Arbitrary Substrates", ACSNano, vol. 4, No. 2, pp. 1108-1114, published Jan. 25, 2010 (in English; cited in parent U.S. Appl. No. 14/647,397).
Zhang et al., "Graphene Oxide as a Matrix for Enzyme Immobilization", Langmuir, vol. 26 (9), pp. 6083-6085, published Mar. 18, 2010 (in English; cited in parent U.S. Appl. No. 14/647,397).

* cited by examiner

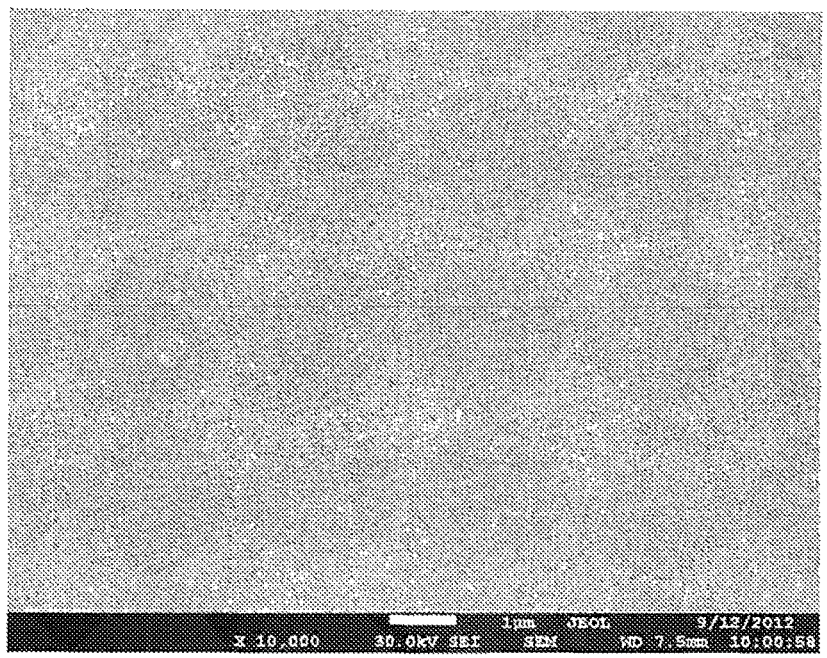

Fig. 8

| Comparison of the biological sensors comprising the film of hydrogel and the film of graphene oxide as an intermediate binding layer | | |
|---|---|---|
| Substrate | Borosilicate glass (thickness of 0.4 mm) with deposited thin film of titan (thickness of 2 nm) | Borosilicate glass (thickness of 0.4 mm) with deposited thin film of titan (thickness of 2 nm) |
| Metal film | Gold (thickness of 40 nm) | Gold (thickness of 40 nm) |
| Intermediate binding layer | Hydrogel (thickness of 150 nm) | Graphene oxide (thickness of 20 nm) |
| Biospecific layer | Streptavidin | Streptavidin |
| Analyte | Biotinylated DNA | Biotinylated DNA |
| Response, a.u. | 409 | 570 |

Fig. 9

BIOLOGICAL SENSOR AND A METHOD OF THE PRODUCTION OF BIOLOGICAL SENSOR

CROSS REFERENCE

This application is a divisional of U.S. application Ser. No. 14/647,397 filed on May 26, 2015, which is a U.S. national stage of International Application No. PCT/RU2013/001100 filed on Dec. 9, 2013, which claims priority of Russian Federation Patent Application No. 2013107267 filed on Feb. 20, 2013, the entire contents of each of the foregoing being hereby incorporated by reference.

TECHNICAL FIELD

The invention relates to the field of biotechnology, namely to the devices for the investigation of biomolecular interactions and for the sensing of biomolecules using a surface plasmon resonance and to the methods of their production. Surface plasmon resonance is a phenomenon of excitation of surface plasmons under the influence of light. It occurs near the metal surface under the condition of attenuated total reflection. The term of "surface plasmon resonance" is related to the optical phenomena allowing to analyze interactions in real time sensing the properties of analyzing media on a matrix and their changes.

The method of biosensing using surface plasmon resonance have several advantages comparing to existing methods such as label-free biosensing without using of radioactive and fluorescent labels, and makes possible to gain a high sensitivity of biosensors based on this method and a high rate of conducted measurements. The proposed invention is related to the devises with sensing surfaces for chemical reactions.

DESCRIPTION OF PRIOR ART

Several technical solutions are known from the prior art.

For example the biological chips for biosensor manufacturing and analysis of biological interactions are known according to U.S. Pat. No. 5,242,828 and consists of three layers: a substrate, a metal film, and a monolayer of biomolecules for adsorbing of a binding partner of an analyte. These biological chips can be used for biosensors based on a surface plasmon resonance. Used in this case biomolecules have the special structure. The limitation of this method is a low number of active centers for biomolecule adsorption due to the planar structure of the biolayer. Also the limitation is the complexity of this device production due to low availability of necessary biomolecules on the market, and processes of their synthesis include many steps and need many reagents. Also the limitation is complexity of biosensors construction based on these devices because for adsorption molecules of a binding partner of an analyte must possess specific functional groups, therefore in every case methods of activation must be developed that limits the class of analyzing molecules.

Moreover, biological sensor according to patent GB 2459604 is known and consists of the following layers: a substrate, a metal film, a film based on amorphous carbon, and a layer of biomolecules. This biosensor allows realizing photolithographic process of molecule organizing. The patent also includes the method of biosensing using this devise and the method of its creation. The limitation of this device is a decrease in sensitivity due to the influence of the carbon film on electromagnetic properties of surface plasmon waves and their adsorption. Also the primary method of binding of biomolecules with films of amorphous carbon is the formation of C—C chemical bonds due to absence of a crystal lattice that limits available for analysis biomolecules and requires development of activation methods for every case.

Also biosensor is known from a prior art according to EP 2216642 A1, which consists of the metal layer with embedded diamond particles. The limitations of this device are complexity of its manufacturing due to usage of complex composite structures and reduction of sensitivity due to low surface area for biomolecule adsorption defined by area of opened diamond particles.

Moreover, multilayer structure is known according to the article "Graphene-based high-performance surface plasmon resonance biosensors" and consists of a metal film covered with a thin layer of graphene. This structure allows to investigate the reaction between biological molecules and graphene, however it is not possess the property of bioselectivity, that makes it unsuitable for the investigation of chemical reactions. In this article graphene film is used as an external surface which interacts with all types of biomolecules in a solution.

The device described in the U.S. Pat. No. 5,763,191 is chosen as a prototype of the proposed invention. This is the universal binding film which is used for analysis of specific biological interactions and consists of a metal film or a film based on metal oxide, and a layer of biological reagent attached to the surface of metal or metal oxide by thiol, disulfide, or phosphine groups of the binding molecule. This biological layer is capable chemically interact with other biological molecules and it can be used for manufacturing of biological sensors based on a surface plasmon resonance. Also this patent includes the method of the analysis using the considered device and the method of its manufacturing.

The limitation of the prototype is the complexity of manufacturing of the layer of biomolecules requiring the synthesis of compounds comprising necessary functional groups and capable to attach to gold surface. Also the limitation is the complexity of attachment of molecules of binding partner of analyte to this layer requiring the development of special methods of activation with focus on the reaction through certain functional groups. This implies that the activation method will work only with certain class of analytes that limits possible applications of the device. Besides, the surface of the metal film of the proposed device is exposed to the influence of an external environment that imposes restrictions on work conditions and chemical reagents used in biosensing. All these limitations cannot provide a high sensitivity together with a specificity of biosensing.

SUMMARY OF THE INVENTION

Technical problem which is solving in the present invention is the creation of a highly sensitive and universal biological sensor with high specificity for biosensing based on a surface plasmon resonance.

This technical problem is solved by the biological sensor (FIG. 1-4) for use in biosensing based on surface plasmon resonance. The biosensor consists of the multilayer structure, which includes a substrate (1), that covered with a thin metal film (2), on the external surface of which an intermediate binding layer (3) is deposited. The intermediate binding layer (3) is performed from the thin film of graphene with the thickness of 0.3-2000 nm, or the thin film of single-walled or multi-walled carbon nanotubes with the thickness of 0.4-2000 nm, or the thin film of graphene oxide with the thickness of 0.7-2000 nm. The biospecific layer (4) is deposited conformally and homogeneously on the surface of the intermediate binding layer (3). The biospecific layer (4) is capable of specific chemical reacting with a certain type of biological molecules of an analyte.

The metal film may be produced from such metals as gold, silver, copper, and aluminum, and its thickness can be equal 10-150 nm. The biospecific layer (4) may contain molecules of a binding partner of an analyte (5). Also the biospecific layer (4) may contain molecules of a binding partner of an analyte (5) and molecules with a high affinity to a binding partner of an analyte (7) and forming a chemical bond with them. Moreover, the biospecific layer may contain the hydrogel (7) with pre-immobilized molecules of a binding partner of an analyte (5). Also the biospecific layer can contain the hydrogel (7) with pre-immobilized molecules of a binding partner of an analyte (5) and the molecules with a high affinity to a binding partner of an analyte (7) and forming a chemical bond with them. The hydrogel of the biospecific layer (4) can be a polysaccharide. The polysaccharides can consist of agarose, alginic acid, dextran, carrageenan, starch, cellulose or derivatives thereof. The derivatives of dextran in the biospecific layer can consist of for example a carboxymethylated dextran. Also the molecules with a high affinity to the molecules of a binding partner of an analyte in the biospecific layer can contain avidin, streptavidin, and deglycosylated avidin, in this case the molecules of a binding partner are biotinylated. The pairs of an analyte and a binding partner to it can consist of the pairs of receptor-ligand, antigen-antibody, enzyme-substrate. The binding parent of an analyte may be an antibody, and a fragment of an antibody to an analyte, and a receptor of an analyte. Moreover, the binding partner of an analyte can be the binding partner of proteins, lipids, DNAs, RNAs, viruses, cells, bacterias, and toxins, and also the modifications of these substances.

The usage in the proposed device of the thin films of graphene, graphene oxide, single-walled and multi-walled carbon nanotubes performing the function of an intermediate binding layer allows the adsorption of a large class of biological molecules, that makes possible the usage of the considered devise for different applications and protects the metal surface from harmful effects of the environment. So in biosensing reagents which can damage the surface of a metal can be used, and also such plasmonic materials as silver can be used.

The inventive method of the production of the biosensor is that the method comprises the following steps:
a) the step of deposition of the metal film (2) on the substrate (1);
b) the step of applying to the outer surface of the metal film of the intermediate binding layer (3) performed as the thin film of graphene with the thickness of 0.3-2000 nm, or the thin film of single-walled or multi-walled carbon nanotubes with the thickness of 0.4-200 nm, or the thin film of graphene oxide with the thickness of 0.7-2000 nm;
c) the step of the biospecific layer (4) deposition, which is conformally and homogeneously adsorbed on the surface of the intermediate binding layer (3) due to the chemical interaction between molecules of the intermediate binding layer (3) and the molecules of the biospecific layer (4). This interaction is due to the stacking interaction or the interaction between the molecules of the biospecific layer (4) with the functional groups of graphene, single-walled or multi-walled carbon nanotubes, or graphene oxide, wherein during the adsorption a large number of the adsorption centers is created on the surface of the intermediate binding layer (3) with the 15-100% degree of filling of the area of the intermediate binding layer by the molecules of the biospecific layer.

The metal film (2) can be the film of gold, silver, copper, or aluminum with the thickness of 10-150 nm.

The biospecific layer (4) can consist of the layer of the molecules of a binding partner of an analyte.

Also the biospecific layer (4) can consist of the layer of the molecules of a binding partner of an analyte and the molecules with a high affinity to the molecules of a binding partner of an analyte and forming a chemical bond with them.

Also the biospecific layer (4) can consist of the layer of the hydrogel (7) with immobilized molecules of a binding partner of an analyte (5).

Also the biospecific layer (4) can consist of the layer of the hydrogel (7) with immobilized molecules of a binding partner of an analyte and the molecules with a high affinity to the molecules of a binding partner of an analyte and forming a chemical bond with them.

Also polysaccharides is appropriate to use as the hydrogel (7). Agarose, alginic acid, dextran, carrageenan, starch, cellulose or derivatives thereof is preferable to use as hydrogel (7). As derivatives of dextran the biospecific layer can contain a carboxymethylated dextran. As the molecules with a high affinity to the molecules of a binding partner of an analyte the molecules of avidin, streptavidin, and deglycosylated avidin can be deposited, in this case the molecules of a binding partner are biotinylated.

The interaction of the molecules of the biospecific layer (4) with the functional groups of graphene, single- or multi-walled carbon nanotubes, or graphene oxide can be performed by the interaction with the functional groups such as epoxy, hydroxyl, carbonyl or carboxyl groups. As a binding partner of an analyte an antibody, an antibody fragment to an analyte, or an analyte receptor can be used. Furthermore, as the binding partner of a analyte can consist of the binding partner of proteins, lipids, DNA, RNA, viruses, cells, bacteria or toxins, as well as chemical modifications of the above substances.

LIST OF FIGURES

On FIG. 1 the general view if the biological sensor (side flew) is shown.

Figure 2:
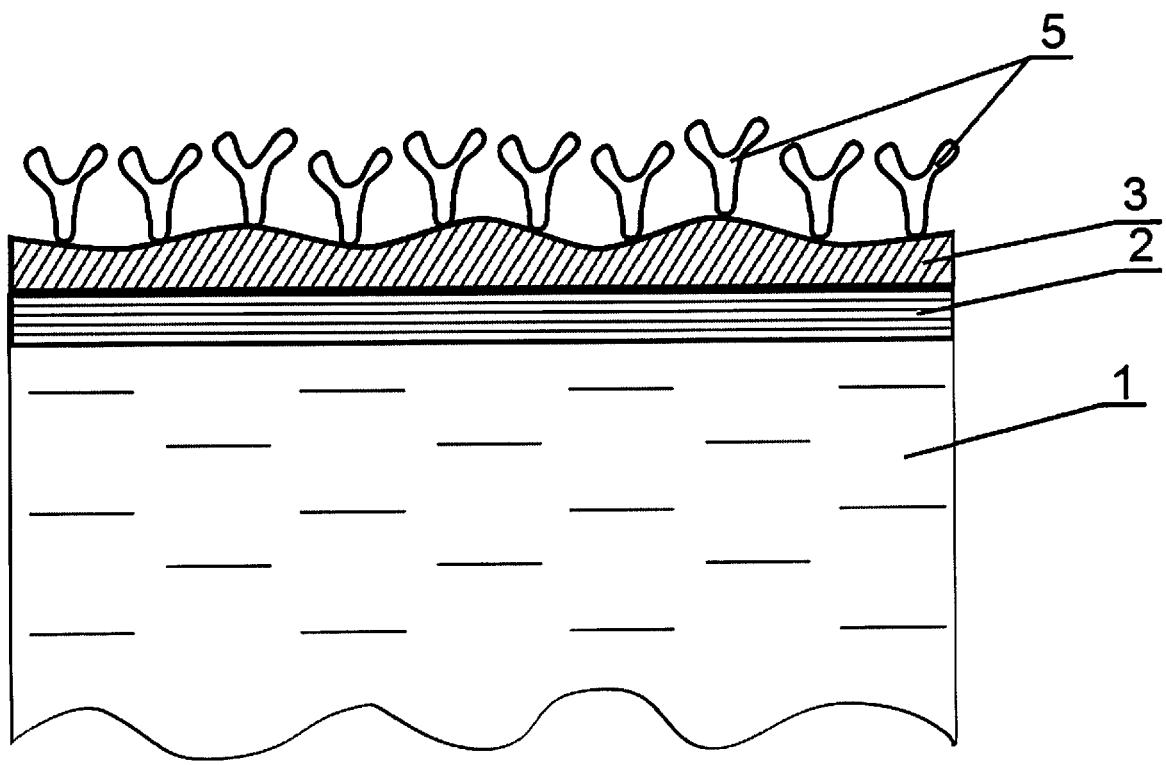

On FIG. 2 the biological sensor with the biospecific layer (4) containing the molecules of a binding partner of an analyte (5) is shown.

Figure 3:
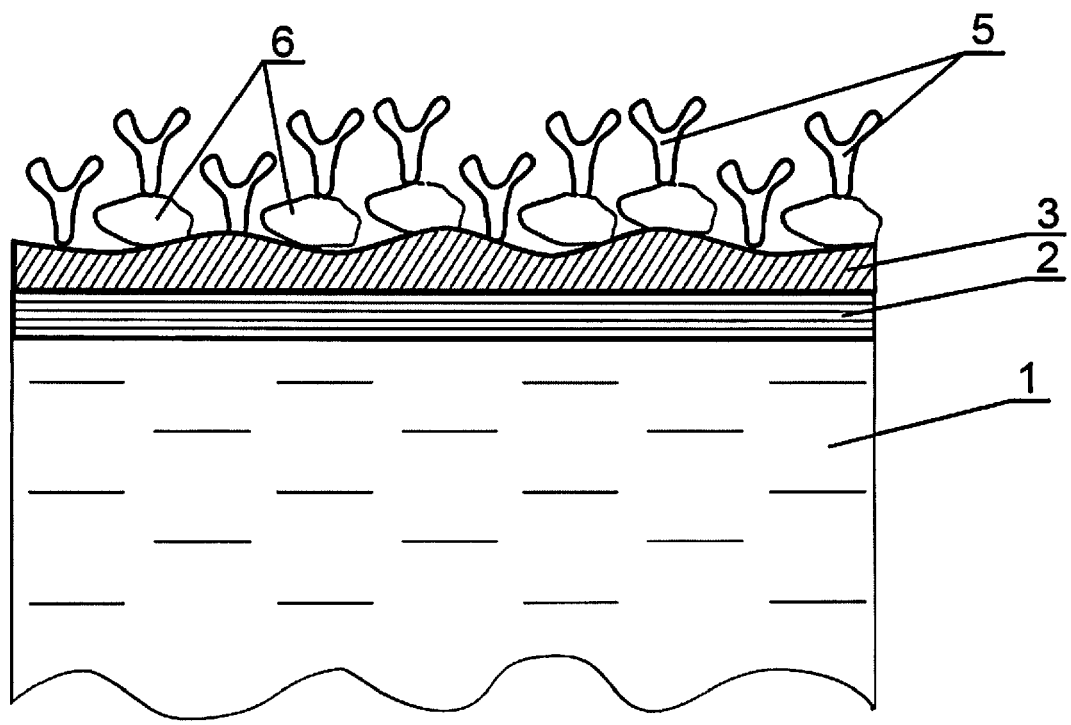

On FIG. 3 the biological sensor with the biospecific layer (4) containing the molecules of a binding partner of an analyte (5) and the molecules capable of forming a chemical bond with the molecules of a binding partner (6) is shown.

Figure 4:
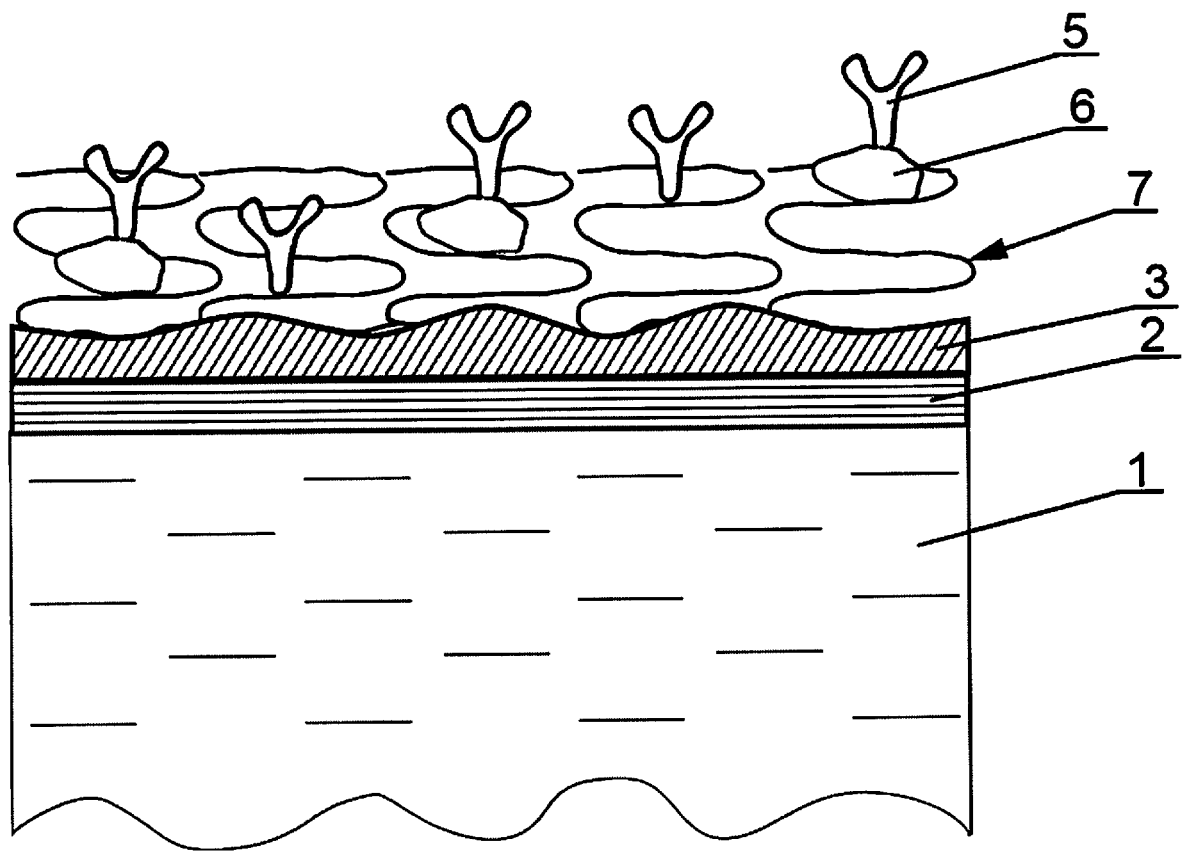

On FIG. 4 the biological sensor with the biospecific layer (4) containing the hydrogel with the immobilized molecules of a binding partner of an analyte (5) and the molecules capable of forming chemical a bond with the molecules of a binding partner (6) is shown.

Figure 5:
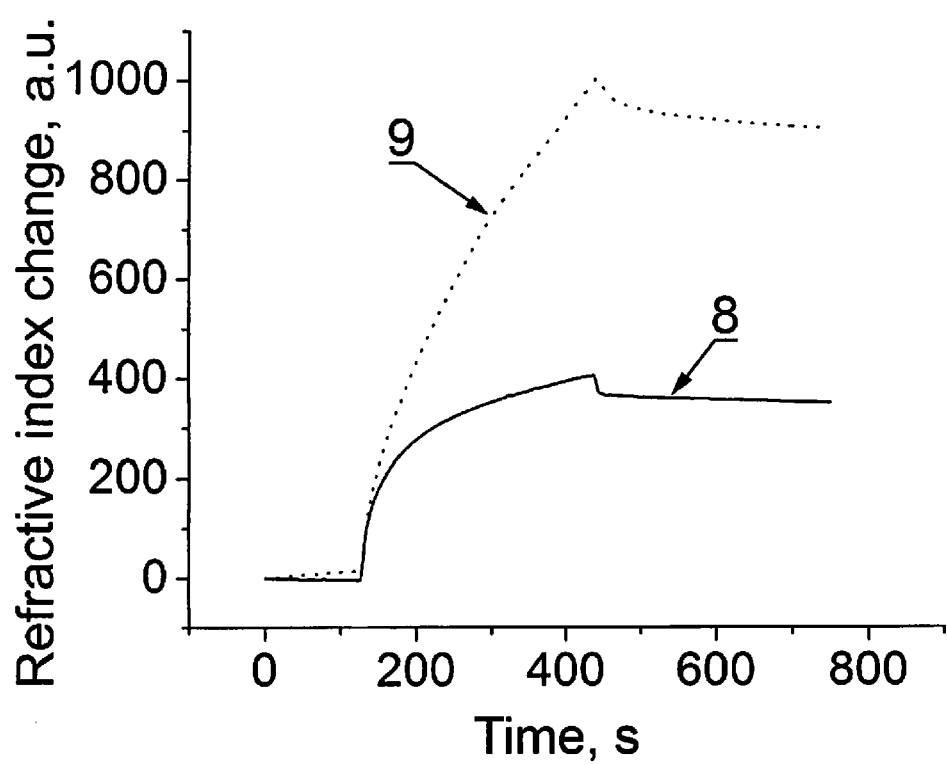

On FIG. 5 the kinetic curve of adsorption of the biotinylated oligonucleotide molecules adsorption on the surface of the thin film of graphene oxide and on the surface of biological sensor comprising of three layers: the substrate, the metal film, and the carboxymethylated dextran with the immobilized molecules of streptavidin is shown.

Figure 6:
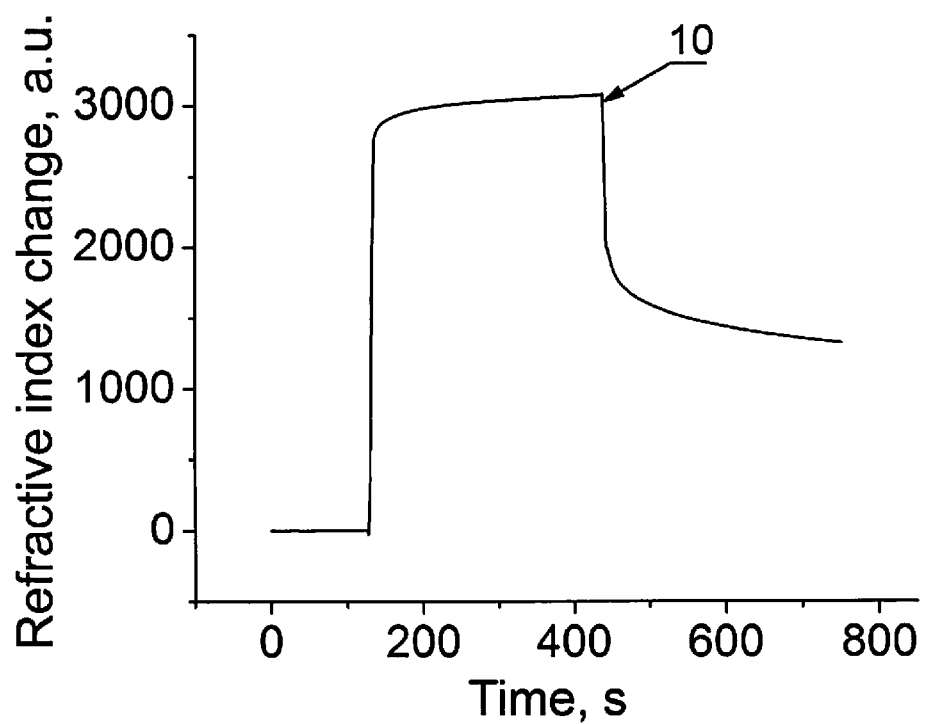

On FIG. 6 the kinetic curve of adsorption of the molecules capable of forming a chemical bond with the molecules of a binding partner of an analyte on the biological sensor based on the thin film of graphene oxide is shown.

Figure 7:
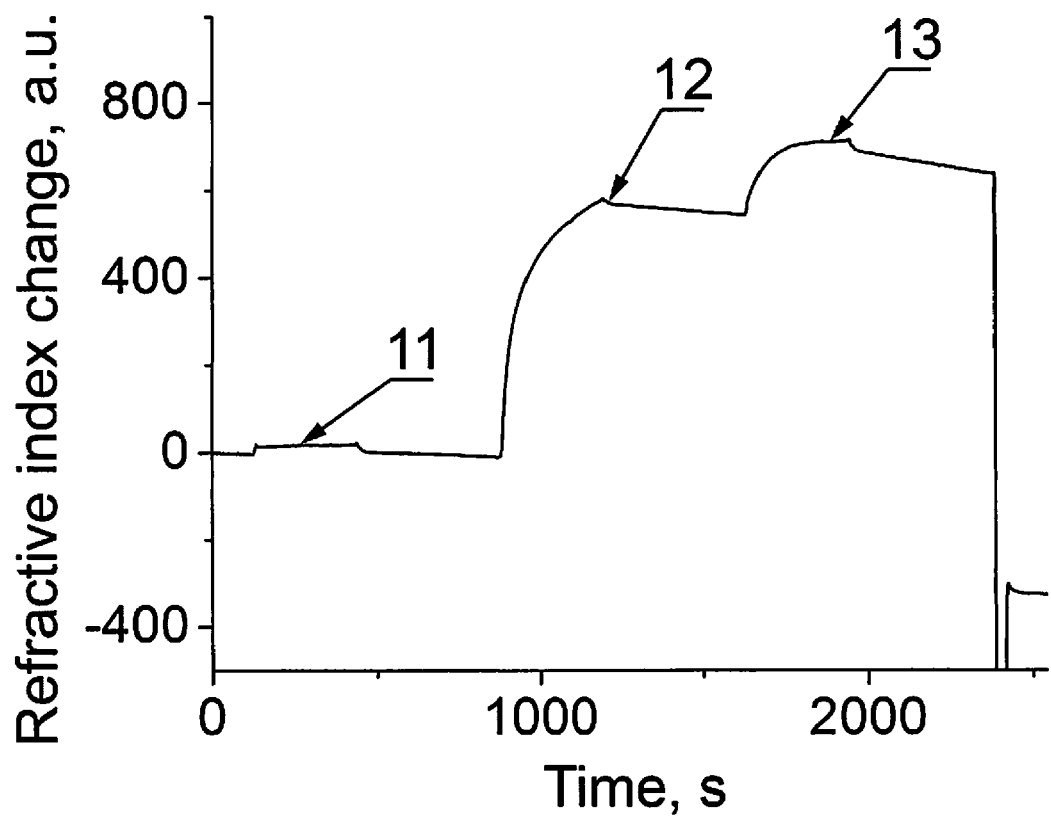

On FIG. 7 the kinetic curve of adsorption of the oligonucleotides on the surface of the biospesific layer with the immobilized molecules of streptavidin is shown.

On FIG. 8 the raster electronic microscopy image of the thin film of graphene oxide deposited on the surface of the metal film is shown.

On FIG. 9 the comparative table of experimental data obtained by the biological sensors containing as the intermediate binding layer thin film of the hydrogel and the thin film of graphene oxide is shown.

DESCRIPTION OF THE PREFERRED EMBODIMENTS

The biological sensor (FIG. 1) consists of a substrate (1), a metal film (2), which is covered by the intermediate binding layer (3) made of the thin film of graphene, the thin film of graphene oxide, or the thin film of carbon nanotubes. The biospecific layer (4) is conformally and homogeneously adsorbed on the surface of layer (3). The layer of the molecules of a binding partner of an analyte (5) (FIG. 2) or the layer of the complex of the molecules capable chemically bind with the molecules of a binding partner of an analyte and chemically bond with them (FIG. 3) can be used as the biospecific layer. Also the hydrogel (7) (FIG. 4) with the immobilised molecules of the molecules of a binding partner of an analyte (5) and/or the complex of the molecules of a binding partner of an analyte and the molecules capable of chemically bind with them (6) can be used as the biospecific layer. FIG. 5 shows the kinetic curve of adsorption of the biotinylated oligonucleotides on the surface of the intermediate binding laayer of the biosensor based on the thin film of graphene oxide (curve 8) and on the surface of biological sensor consisting the following layers: the substrate, the metal film, and the biospecific layer with the hydrogel (carboxymethylated dextran) and streptavidin molecules (curve 9). The horizontal axis is time, the vertical axis is the change of the refractive index of the medium near the adsorption surface, which is proportional to the mass of molecules adsorbed on the surface. Therefore, we can conclude that the film based on graphene oxide has better adsorption properties than the layers containing hydrogel. FIG. 6 shows the graph of streptavidin molecule adsorption on the biological sensor based on the thin film of graphene oxide.

FIG. 7 shows the graph of oligonucleotide adsorption on the biological sensor comprising the substrate made of the borosilicate glass with the thickness of 0.4 nm which surface is covered by the titan film with the thickness of 2 nm. The substrate is covered by the gold film with the thickness of 40 nm. The intermediate binding layer of graphene oxide with the thickness of 20 nm and the biospecific layer are deposited on the gold film. The biospecific layer consists of streptavidin moilecules, which form a stable complex with the molecules having a biotin residue. Streptavidin was adsorbed during 10 minutes from the solution with the concentration of 50 ug/ml on the surface of the intermediate binding layer in the flow cell. Three peaks on graph correspond to the adsorption of oligonucleotides: 11, 13—without biotin residue, 12—with biotin residue. Oligonucleotides used in the cases 11, 13 and in the case 12 are complimentary and can form a bind with each other. Smallness of the peak 11 indicates a high specificity of the obtained biological sensor, which means that the biological sensor interacts only with certain types of molecules. FIG. 8 shows the image of the graphene oxide layer on the surface of the metal film, obtained using raster electron microscopy. The data in table (FIG. 9) are based on the experimental results and compares biological sensors comprising the thin layer of hydrogel with the thickness of 150 nm and the thin layer of graphene oxide with the thickness of 20 nm as intermediate binding layers. The signal of the biological sensor comprising film of the hydrogel obtained during the sensing of biotinylated DNA and which is proportional to the change of the refractive index of the media near the surface of the biological sensor is 409 arbitrary units. In the case of the biological sensor comprising the film of graphene oxide the signal is 570 arbitrary units. Thus, the response and, therefore, the sensitivity of the biological sensor comprising the thin film of graphene oxide as the intermediate binding layer is 40% higher.

The device operates as follows. The solution of an analyte is supplied to the biospecific layer (4) of the biological sensor by means of a flow cell or a cuvette. Wherein, the chemical reaction is carried out between an analyte and the molecules of the biospecific layer (4) represented by the molecules of a binding partner of an analyte (5) attached to the surface of the intermediate binding layer directly or using the biological molecules (6) capable to form a chemical bond with the molecules of a binding partner of an analyte and/or the hydrogel (7) deposited on the surface of the biological sensor. Further, required parameters of this reaction are obtained using the method of biosensing based on a surface plasmon resonance. The essence of the method is to detect in various ways the changes of the resonant conditions of the surface plasmon excitation in the metal layer (2) caused by the changes of the effective refractive index of the media near the surface due to attaching of biomolecules. The most popular in commercial devices way of the surface plasmon excitation is proposed by Kretschmann [6]. According to this, a laser beam is falling under certain angle on the metal film (1) from the substrate side (1) and excites surface plasmons on the border of the metal film (2) and the media containing analyte. Wherein the optimal thickness of metal film (2) is in the range of 10-150 nm. The upper border is explained by the fact, that at higher values of the film thickness the failure in reflection is small, which greatly affects the sensitivity of the method. At the thicknesses of the film (2) less than 10 nm the form of the resonant curve corresponding to the surface plasmon resonance changes due to the change of the waveguide mode of the surface plasmon. Further, the information about the refractive index change of the media near the metal film is obtained basing on the value of the resonant angle, phase shift of the reflected beam, or the changes of the intensity of the reflected beam. It does not make sense to deposit the intermediate binding layer (3) with the thickness greater than 2000 nm on the surface of the metal film (2) because of the penetration depth of the electromagnetic field of the surface plasmon is about 500 nm, therefore, molecules located at a distance greater than 2000 nm have little effect on conditions of a surface plasmon excitation and hence it cannot be detected. The intermediate binding layer (3) with the thickness greater than 2000 nm, in turn, hinders the access of the analyte in the region, where it can be detected. The minimal thickness of the intermediate binding layer comprising graphene corresponds to the monomolecular layer which the thickness is assumed to be equal 0.3 nm [7]. For the intermediate binding layer (3) comprising graphene oxide the minimum possible thickness corresponded to the monomolecular layer equals 0.7 nm [8]. For the intermediate binding layer (3) comprising carbon nanotubes the minimum possible thickness equals the diameter of carbon nanotubes which can be equal to 0.4 nm [9]. Molecules of proteins, lipids, DNA, RNA, viruses, cells, bacterias, and toxins can be used as analytes for the biological sensor.

The method of production of the biological sensor is realized as following:

The metal film (2) is deposited on the substrate (1) using for example electron beam deposition. So, for example, to deposit gold film with the thickness of 40 nm as a substrate the plate of borosilicate glass with the deposited titan film with the thickness of 2 nm is used. Further deposition of gold on the substrate is conducted in the vacuum chamber at the pressure of $10^{-7}$ Torr, the accelerating voltage of electrons of 4 kV, and the temperature of 150 degrees Celsius. The thickness and optical properties of the gold film are controlled by means of ellipsometric measurements.

Further the intermediate binding layer (3) in the form of the thin film of graphene, graphene oxide, or single-walled or multi-walled carbon nanotubes is deposited on the surface of the metal film (the image of the graphene oxide film obtained using rater electron microscopy is shown on FIG. 8). A thin film of graphene, graphene oxide, or single-walled or multi-walled carbon nanotubes are deposited using the solution of the respective substance, which is further filtrated by the cellulose membrane. After the filtration process the membrane is placed on the surface of the metal film and dissolved in acetone leaving the thin film of graphene, graphene oxide, or carbon nanotubes. So for example for the deposition of the intermediate binding layer containing the thin film of graphene oxide with the thickness of 20 nm 1 ml of graphene oxide solution in water with the concentration of 5 ug/ml is used.

The next step of the biological sensor creation is the stage of biospecific layer (4) deposition on the intermediate binding layer in which such molecules comprising the biospecific layer as molecules of the partner of an analyte (5), the molecules capable chemically bind with the molecules of the partner of an analyte (6), or the hydrogel are deposited directly from the solution. The solution with biomolecules is brought in a contact with for example a flow cell or a cuvette. FIG. 6 shows the adsorption of the streptavidin molecules which are the binding partner of the molecules with the biotin residue using a flow cell. At the same moment a time of adsorption is selected so that biological molecules occupy large number of adsorption centers on the surface of graphene, graphene oxide, or carbon nanotubes eliminating in further nonspecific binding of analyte molecules with the surface of the biological sensor. Wherein usage of special substances except molecules themselves are not required for manufacturing of such films. So for example for adsorption of the biospecific layer containing streptavidin molecules on the surface of graphene oxide film these molecules are adsorbed from the solution with the concentration of 10 ug/ml using the flow cell during 10 minutes. Subsequently the quality can be checked by using a test sample, which is known that molecules from its structure should not interact with the obtained biological layer. The kinetic curve (12) of biotinylated DNA deposition on the obtained biosensor comprising streptavidin molecules is shown on the FIG. 7. The smallness of the peak (11) reflecting the interaction of the nonbiotinylated molecules with the streptavidin layer shows a sufficient level of negligibility of nonspecific interactions.

The proposed device and method of its production provide in comparison with the known level of technique the following results: a high sensitivity of biosensor in combination with a high biospecificity; the protection of metal film from an environmental exposure that allows to use in the biosensing reagents that may damage the metal surface, and also to use such plasmonic materials as silver easily degrading under an environmental exposure; the possibility to detect large biological objects.

Thus the new relationship of known properties and a set of distinctive properties of the proposed biosensor and method of its creation allows creation of a highly sensitive and universal biological sensor for the biosensing based on the surface plasmon resonance.

The proposed device and a method of its production can be used for monitoring and recording of the concentration of chemical and biochemical substances and for the definition of parameters of biomolecular reactions in different industrial processes using biological materials.

The proposed invention can be also used in the pharmaceutical industry for the investigation of pharmacological properties and for the determination of a chemical composition of developing drugs.

Moreover, the developed device and a method of its production can be used in processes of a quality control of food products.

REFERENCES CITED

1. U.S. Pat. No. 5,242,828;
2. Patent GB 2459604;
3. Description to the patent EP 2216642 A1;
4. Wijaya E., Maaloulib N., Boukherroubb R., Szuneritsb S., Vilcota J-P., "Graphene-based high-performance surface plasmon resonance biosensors", Proceedings of SPIE, Vol. 8424, 84240R, 2012;
5. U.S. Pat. No. 5,763,191;
6. Schasfoort R. B. M., Tudos A. J., Handbook of Surface Plasmon Resonance, RCS Publishing, Cambridge, 2008.
7. Blake P., Hill E. W., Castro Neto A. H., Novoselov K. S., Jiang D., Yang R., Booth T. J., and Geim A. K., "Making graphene visible", Appl. Phys. Lett., Vol. 91, 063124, 2007.
8. Pandey D., Reifenberger R., Piner R., "Scanning probe microscopy study of exfoliated oxidized graphene sheets", Surface Science, V. 602, pp. 1607-1613, 2008.
9. Guan L., Suenaga K., and Iijima S., "Smallest Carbon Nanotube Assigned with Atomic Resolution Accuracy", Nano Letters, Vol. 8, pp. 459-462, 2008.

Therefore, the following is claimed:

1. A method for producing a biological sensor, the method comprising:

a) depositing a gold film onto a first surface of a substrate, the gold film having a thickness in a first range of from 10 nm to 150 nm and comprising an outer surface opposite to the substrate, b) depositing an intermediate binding layer onto the outer surface of the gold film, c) depositing a biospecific layer onto a second surface of the intermediate binding layer, the second surface being opposite to the substrate, wherein the intermediate binding layer consists of a film of graphene oxide having a thickness in a second range of from 20 nm to 2000 nm, and wherein the biospecific layer is adsorbed conformally and homogeneously on the second surface of the intermediate binding layer due to first chemical interaction forces between the intermediate binding layer and the biospecific layer, wherein the biospecific layer fills between 15% and 100% of the second surface of the intermediate binding layer, wherein the biospecific layer is adapted for a specific second chemical interaction with a certain type of biological molecules of an analyte.

2. The method for producing according to claim 1, wherein the depositing the gold film onto the first surface of the substrate is conducted in a vacuum chamber by an electron beam deposition.

3. The method for producing according to claim 2, comprising controlling the thickness of the gold film using ellipsometric measurements.

4. The method for producing according to claim 3, comprising controlling optical properties of the gold film using ellipsometric measurements.

5. The method for producing according to claim 4, wherein the depositing the intermediate binding layer onto the outer surface of the gold film comprises following subsequent stages of:
    a) preparing a graphene oxide solution,
    b) after the preparing, filtering the graphene oxide solution by a cellulose membrane,
    c) after the filtering, placing the cellulose membrane onto the outer surface of the gold film,
    d) after the placing, dissolving the cellulose membrane in acetone in view to leave the intermediate binding layer consisting of the film of graphene oxide onto the outer surface of the gold film.

6. The method for producing according to claim 5, comprising checking a quality of the biospecific layer using a test sample, the quality being representative of a predetermined level of negligibility of nonspecific interactions of the biospecific layer.

7. The method for producing according to claim 6, wherein the depositing the biospecific layer onto the second surface of the intermediate binding layer comprises following subsequent stages of:
    preparing a biospecific solution of first molecules of a binding partner of the analyte,
    after the preparing, bringing the biospecific solution in a contact with the second surface of the intermediate binding layer using a flow cell.

8. The method for producing according to claim 7, wherein the biospecific solution further comprises:
    (i) second molecules having an affinity to the first molecules of the binding partner of the analyte, the second molecules being adapted to form a chemical bond with the first molecules of the binding partner of the analyte; or
    (ii) a first hydrogel comprising immobilized therein the first molecules of the binding partner of the analyte; or
    (iii) a second hydrogel comprising immobilized therein both the first molecules of the binding partner of the analyte and the second molecules having an affinity to the first molecules of the binding partner of the analyte, the second molecules being adapted to form a chemical bond with the first molecules of the binding partner of the analyte.

9. The method for producing according to claim 7, wherein the biospecific solution further comprises:
    a first hydrogel comprising immobilized therein the first molecules of the binding partner of the analyte, or
    a second hydrogel comprising immobilized therein both the first molecules of the binding partner of the analyte and second molecules having an affinity to the first molecules of the binding partner of the analyte, the second molecules being adapted to form a chemical bond with the first molecules of the binding partner of the analyte,
    wherein each hydrogel chosen between: (a) the first hydrogel, (b) the second hydrogel, comprises polysaccharides.

10. The method for producing according to claim 9, wherein the polysaccharides in the biospecific solution comprise agarose, alginic acid, dextran, carrageenan, starch, cellulose or derivatives thereof.

11. The method for producing according to claim 10, wherein the derivatives of dextran in the biospecific solution comprise carboxymethylated dextran.

12. The method for producing according to claim 7, wherein the biospecific solution further comprises:
    second molecules having an affinity to the first molecules of the binding partner of the analyte, the second molecules being adapted to form a chemical bond with the first molecules of the binding partner of the analyte; or
    a second hydrogel comprising immobilized therein both the first molecules of the binding partner of the analyte and the second molecules having an affinity to the first molecules of the binding partner of the analyte, the second molecules being adapted to form a chemical bond with the first molecules of the binding partner of the analyte,
    wherein the first molecules of the binding partner of the analyte are biotinylated, and
    wherein the second molecules are chosen from the following molecules: (a) molecules of avidin, (b) molecules of streptavidin, (c) molecules of deglycosylated avidin.

13. The method for producing according to claim 7, wherein the binding partner of the analyte is an antibody or a fragment of the antibody to the analyte, or
    wherein the binding partner of the analyte is a receptor of the analyte, or
    wherein the binding partner of the analyte is a binding partner of proteins, lipids, DNAs, RNAs, viruses, cells, bacteria, or toxins, or chemical modifications of these substances.

14. The method for producing according to claim 1, wherein the film of graphene oxide has a thickness of 20 nm.

15. The method for producing according to claim 1, wherein the film of graphene oxide has a thickness in a range of from 20 nm to 500 nm.

* * * * *